US005404876A

United States Patent [19]
DiSabito et al.

[11] Patent Number: 5,404,876
[45] Date of Patent: Apr. 11, 1995

[54] DISPOSABLE LEG PLATE ASSEMBLY HAVING FLOATING REFERENCE ELECTRODE

[75] Inventors: David M. DiSabito, Clarence, N.Y.; Robert P. Harhen, Andover, Mass.; Robert J. Graumann, Williamsville, N.Y.

[73] Assignee: Graphic Controls Corporation, Buffalo, N.Y.

[21] Appl. No.: 187,631

[22] Filed: Jan. 26, 1994

[51] Int. Cl.6 .............................................. A61B 5/04
[52] U.S. Cl. ...................................... 128/639; 128/644
[58] Field of Search ................ 128/639, 640, 642, 644, 128/698; 607/138; 606/32

[56] References Cited

U.S. PATENT DOCUMENTS

| | | |
|---|---|---|
| 2,590,876 | 4/1952 | Landauer . |
| 2,882,904 | 4/1959 | Rasmussen . |
| 3,464,404 | 9/1969 | Mason . |
| 3,534,727 | 10/1970 | Roman . |
| 3,717,141 | 2/1973 | Krohn et al. . |
| 3,812,845 | 5/1974 | Partridge . |
| 3,888,240 | 6/1975 | Reinhold, Jr. et al. . |
| 3,895,635 | 7/1975 | Justus et al. . |
| 3,973,557 | 8/1976 | Allison . |
| 3,977,392 | 8/1976 | Manley . |
| 3,989,035 | 11/1976 | Zuehlsdorff . |
| 3,993,049 | 11/1976 | Kater . |
| 4,027,664 | 6/1977 | Heavner, Jr. et al. . |
| 4,082,086 | 4/1978 | Page et al. . |
| 4,121,573 | 10/1978 | Crovella et al. . |
| 4,121,575 | 10/1978 | Mills et al. . |
| 4,197,851 | 4/1980 | Fellus . |
| 4,209,020 | 6/1980 | Nielsen . |
| 5,046,965 | 9/1991 | Neese et al. . |
| 5,062,426 | 11/1991 | Ulbrich et al. ........................ 128/640 |
| 5,168,876 | 12/1992 | Quedens ................................. 128/642 |
| 5,197,472 | 3/1993 | DiSabito . |
| 5,199,432 | 4/1993 | Quedens et al. ....................... 128/642 |

OTHER PUBLICATIONS

Berkeley Bio-Engineering "Operating the Berkeley 900 Fetal Monitoring System", 1975, Revised Feb. 23, 1977.

*Primary Examiner*—Lee S. Cohen
*Assistant Examiner*—Brian M. Green
*Attorney, Agent, or Firm*—Ratner & Prestia

[57] ABSTRACT

A disposable electrode assembly for contacting a patient and for receiving electrical signals from at least one remotely located electrode, the remotely located electrode having leads. The electrode assembly has a thin, flexible, leg plate with a bottom surface contacting the patient without adhesive. At least two triangular-shaped springs are carried by the leg plate for electrically and mechanically connecting the leads from the remotely located electrode to the leg plate. At least two latches, each adapted to snap over one of the triangular-shaped springs, provide an audio indication of flap closure and keep a flap closed over each of the triangular-shaped springs. A reference electrode electrically contacts the patient through a skin-contacting surface when the electrode assembly is secured to the patient. The reference electrode is electrically coupled to, but mechanically decoupled from, the leg plate. Separate, insulated wires electrically engage the springs and the reference electrode. The wires are joined in a cord providing electrical connection to an external monitoring device. An attachment member secures the electrode assembly to the patient.

31 Claims, 4 Drawing Sheets

DISPOSABLE LEG PLATE ASSEMBLY HAVING FLOATING REFERENCE ELECTRODE

BACKGROUND OF THE INVENTION

The present invention relates to an electrode assembly and, more particularly, to a disposable leg plate electrode assembly, having a floating maternal reference electrode, which is most useful as part of a fetal monitoring system.

Fetal monitoring is a technique which has been used for many years, primarily when a mother is giving birth. The technique is accomplished by attaching one or more electrodes to the fetus. An additional electrode attached to the mother is used to establish a base or reference voltage for the fetal electrodes. The fetal electrodes, via leads passing through the birth canal, and the reference electrode are connected to a fetal monitoring device.

In order to provide an electrical and mechanical connection between the fetal electrodes and the fetal monitoring device, obtain a maternal reference for reliable signal processing, and prevent disengagement of the fetal electrodes in the event that the mother moves relative to the fetal monitoring device, known electrode assemblies use a metal base plate strapped to the mother's thigh. The plate carries a pair of insulated connectors which engage the leads passing through the birth canal and connecting to the fetal electrodes. A main cable electrically coupled to the metal base plate and to the connectors is used to link the electrode assembly to the fetal monitoring device.

Although the electrode assembly described above has had some success, it has several drawbacks. The most significant of these drawbacks is the risk of cross-contamination presented by the assembly, which operates in an environment filled with body fluids. A related drawback is its expense: the cost of such assemblies normally is between $50 and $200. Moreover, although they may be reused, the assemblies represent a capital investment to a hospital or clinic which cannot be directly charged to the patient. The expense is increased because the plate assemblies become soiled during use and must be cleaned before being reused. In addition, a hospital or clinic would require numerous identical assemblies to assure availability during the cleaning process.

Thus, there is a continuing need for high quality, sanitary, but inexpensive electrode assemblies. For purposes of convenience and safety (e.g., to maintain sterility in a medical environment), the electrode assembly should be sufficiently inexpensive to manufacture that it is practical to dispose of and to replace the electrode assembly after only one use (hence, the electrode assembly must be "disposable").

Conventional electrode assemblies, such as that described above, are relatively complex in their structure. Many of them have hard, bulky components which make them uncomfortable to the patient. They often have a relatively high profile (height). The connectors project from the electrode assembly a significant distance to allow connection of the lead wires from the fetus. A high profile is disadvantageous because it increases the risk of damage by hitting other objects during use and storage. The electrical contacts between the fetus and the connectors and between the reference electrode and the patient are essential; those contacts must be protected from disengagement. Consequently, a low profile electrode is preferable.

Most conventional electrode assemblies suffer from motion artifacts. Motion artifacts can be defined as motion-induced fluctuation of skin potential. Such artifacts create electrical interference which is often superimposed on the bipotential skin signal measured by the electrode, thereby reducing the electrode's usefulness as a diagnostic tool. Motion artifacts have long been a problem in measuring biopotentials. Artifacts are generally caused by movement of the patient relative to the electrode applied to the patient's skin. That movement disturbs the skin potential and creates extraneous output on the monitor which either masks the desired bipotential signal or shifts the base line.

The conventional electrode assemblies are typically attached to the patient on the mother's thigh. That location of attachment and the metal base plate component of the assemblies give such assemblies the name "leg plate." (Although the present invention neither incorporates a metal base plate nor must be attached to the patient's leg, as discussed below, the name "leg plate" is retained for purposes of continuity.) Encircling the thigh and assuring attachment of the conventional assembly are relatively untidy and unsanitary straps. It would be desirable both to avoid these straps and to provide the electrode assembly with sufficient flexibility to permit attachment to the patient at a variety of locations, including the thigh, the abdomen, and other sites.

As the above discussion makes evident, the problem of providing a highly reliable, disposable, low-profile, comfortable electrode assembly which minimizes motion artifacts has presented a major challenge to designers in the labor and delivery health care field. The development of an economical electrode assembly having these qualities would represent a major technological advance in the field. The advantages of such a device would satisfy a long-felt need within the medical profession.

U.S. Pat. No. 4,209,020 issued to Nielsen discloses an electrode assembly which attempts to satisfy that need and to overcome the drawbacks of conventional devices. The Nielsen assembly is disposable and less expensive than those devices described above. Nevertheless, it still has practical problems, the three most significant of which are: 1) the way in which the leads from the remote fetal electrodes are attached to the electrode assembly, 2) the way in which the electrode assembly is attached to the patient, and 3) the way in which the maternal reference electrode is attached to the electrode assembly.

Nielsen uses spring clips to attach the fetal electrode leads to the assembly. These protruding clips give the assembly a high profile and complicate both the use of the assembly and its manufacture. As a general rule, of course, the more complicated the manufacturing procedure, the more expensive the item. Nielsen also uses an adhesive to attach the assembly to the patient. An adhesive attachment on the patient's skin precludes easy adjustment of the assembly, is uncomfortable for the patient, and risks injury to the patient upon removal. Finally, Nielsen fixes the reference electrode to the body of the electrode assembly. Because the maternal reference electrode is mechanically coupled to the assembly, the risk of motion artifact as the mother moves relative to the reference electrode is great.

A vastly improved electrode assembly is disclosed in U.S. Pat. No. 5,197,472 issued to DiSabito. The disposable electrode assembly includes a pair of thin, flexible, foam pads having adhesive on their facing surfaces. Leads from the fetal electrodes are secured between the pads by the adhesive and are in electrical contact with conductive plates also located between the two pads. The lower pad carries a reference electrode, fixed to a conductive plate, which is in electrical contact with the patient when the assembly is attached to the patient. Such attachment is assured without using an adhesive on the lower pad which contacts the patient's skin. The conductive plates and the reference electrode are electrically connected to a fetal monitoring device by thin conductors also secured between the pads by the adhesive. The thin conductors combine in a cable assembly adapted to connect to the fetal monitoring device.

It would be desirable to mechanically decouple the maternal reference electrode from the electrode assembly to reduce motion artifacts. It would also be desirable to provide an electrical and mechanical connection, between the fetal electrode wires and the electrode assembly, which allows quick and easy attachment of the wires, allows multiple attachment to the electrode assembly, and allows one or more of the wires to be removed easily and without disturbing the connection of the remaining wires.

Therefore, to overcome the shortcomings of the existing medical electrode assemblies and to satisfy the need of the medical profession, a new, reliable, disposable, low-profile, comfortable electrode assembly is provided. A primary object of the present invention is to provide an improved electrode assembly which can be manufactured at low cost yet meets the patient's needs, especially comfort and the assurance of a continually functional device. A related object is to provide an electrode assembly which is easy to use.

It is still another object of the present invention to reduce motion artifacts. An additional object is to assure that the electrode assembly has a very low profile. Yet another object of this invention is to allow for quick and easy attachment and detachment, both between the electrode assembly and the patient and between the fetal electrodes and the electrode assembly. Both types of attachment and detachment should be sufficiently simple that they can be done in low lighting.

SUMMARY OF THE INVENTION

To achieve these and other objects, and in view of its purposes, the present invention provides a disposable electrode assembly having a thin, flexible, leg plate with a lower surface contacting the patient without adhesive. At least two triangular-shaped springs are carried by the leg plate for electrically and mechanically connecting the leads from a remotely located electrode to the leg plate. At least two latches, each adapted to snap over one of the triangular-shaped springs, provide an audio indication of flap closure and keep a flap closed over each of the triangular-shaped springs. A reference electrode electrically contacts the patient through a skin-contacting surface when the electrode assembly is secured to the patient. The reference electrode is electrically coupled to, but mechanically decoupled from, the leg plate. Separate, insulated wires electrically engage the springs and the reference electrode. The wires are joined in a cord providing electrical connection to an external monitoring device. An attachment member secures the electrode assembly to the patient.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which.

DETAILED DESCRIPTION

Figure 1:
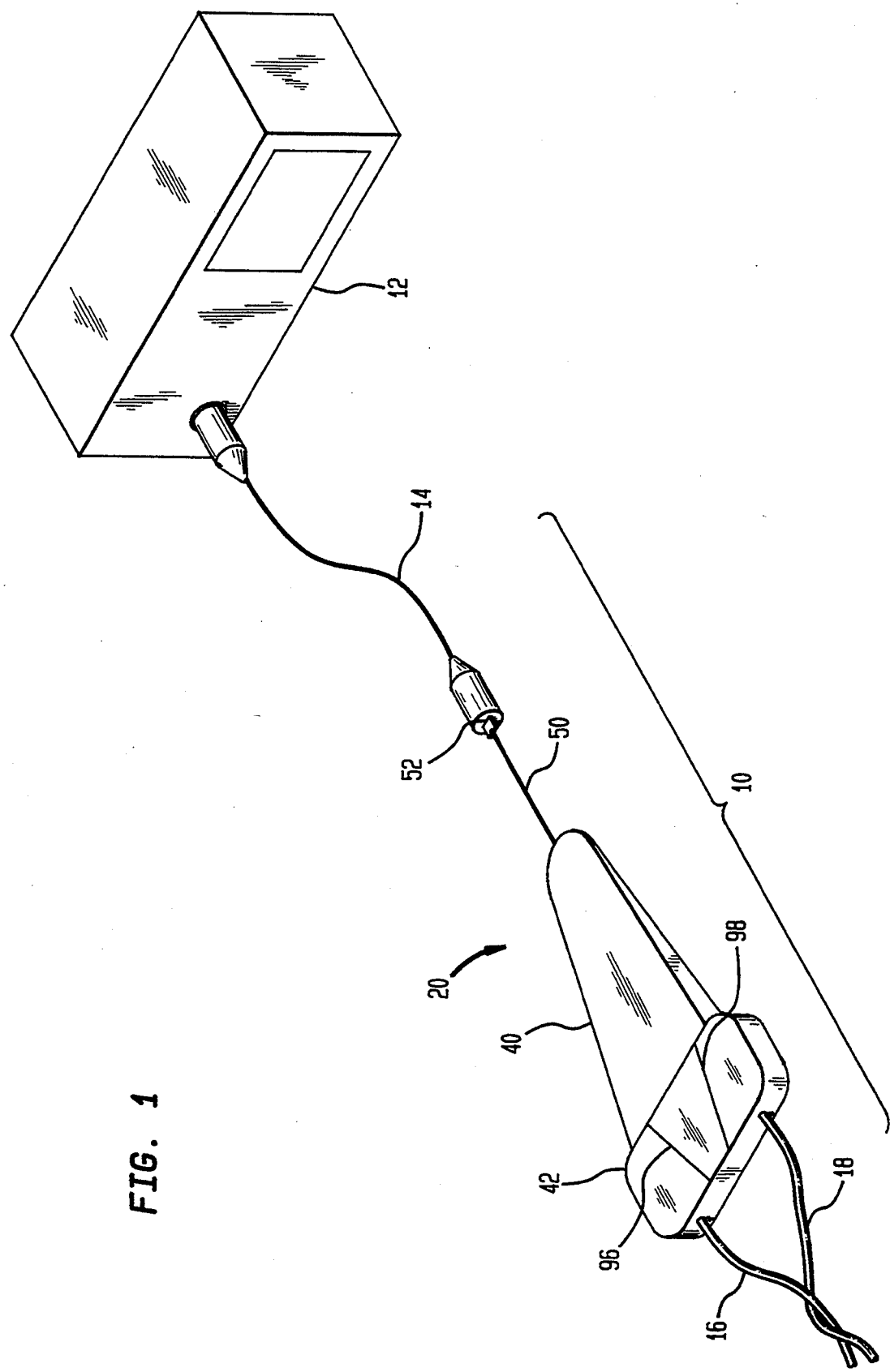
FIG. 1 is a perspective view of an electrode assembly constructed in accordance with the principles of the present invention, illustrating that the assembly is attached to a fetal monitoring device and fetal electrode lead wires.

Like reference numerals have been used throughout the various figures of the drawing to identify like elements. Shown in FIG. 1 is an electrode assembly 10 constructed in accordance with the present invention. Electrode assembly 10 has a leg plate 20 and a cord 50. Cord 50 is connected to leg plate 20 on one end and to a plug 52 on its opposite end. Plug 52 may be a polycarbonate modular connector, commonly used in the telephone industry. Electrode assembly 10 is connected to a fetal monitoring device 12 via cable 14. Shown connected to leg plate 20 of electrode assembly 10 are leads (wires) 16, 18 coming from one or more remotely located fetal electrodes (not shown).

Figure 7:
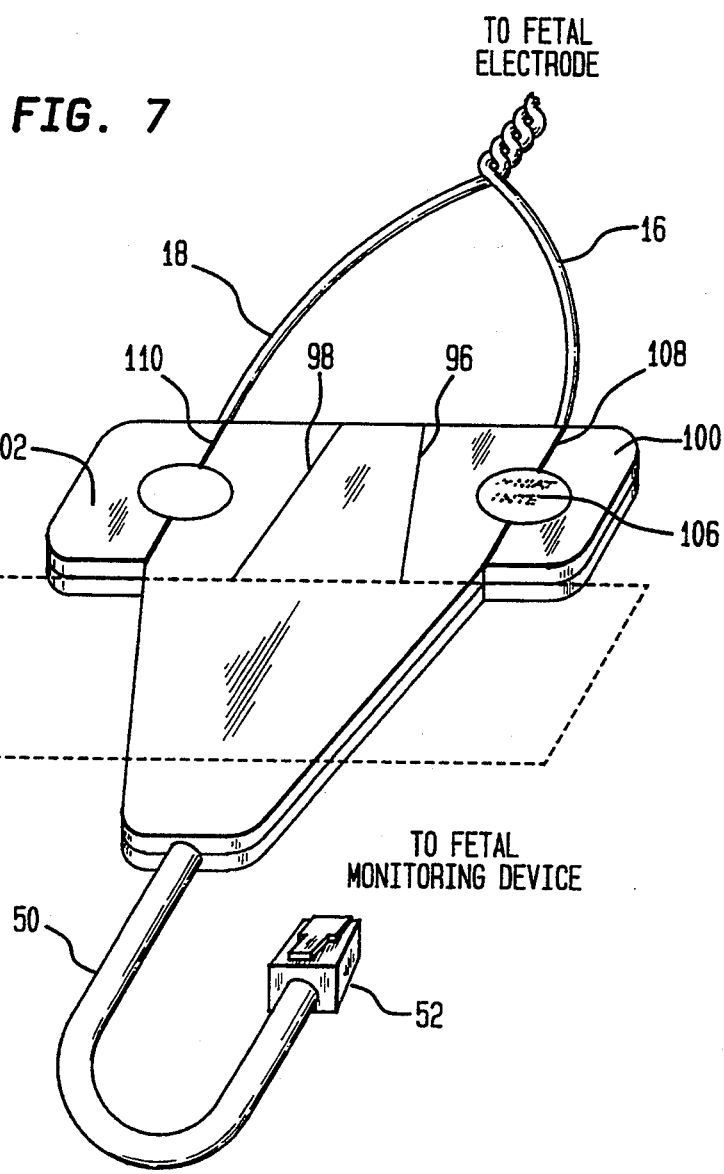
FIG. 7 a perspective view of an electrode assembly constructed in accordance with the principles of the present invention with the fetal electrode lead wires inserted, also showing one embodiment of the structure disclosed for securing the electrode assembly to a patient.

Leg plate 20 may be of any suitable shape. In the preferred embodiment, however, leg plate 20 has a "T" shape formed by a tapered leg 40 and a perpendicular head 42. Leg 40 has a substantially trapezoidal shape. Suitable dimensions for leg 40 are a length of about 2 inches (5 cm), a first base of about 1.5 inches (3.8 cm), and a second base of about 0.5 inches (1.3 cm). Head 42 has a substantially rectangular shape. Suitable dimensions for head 42 are 2.5 inches (6.3 cm) by 1.0 inches (2.5 cm). Thus, head 42 extends beyond leg 40 by about 0.5 inches (1.3 cm) on each side, forming flaps 100 and 102 (see FIG. 7), and the total length of leg plate 20 is about 3 inches (7.6 cm).

Figure 2:
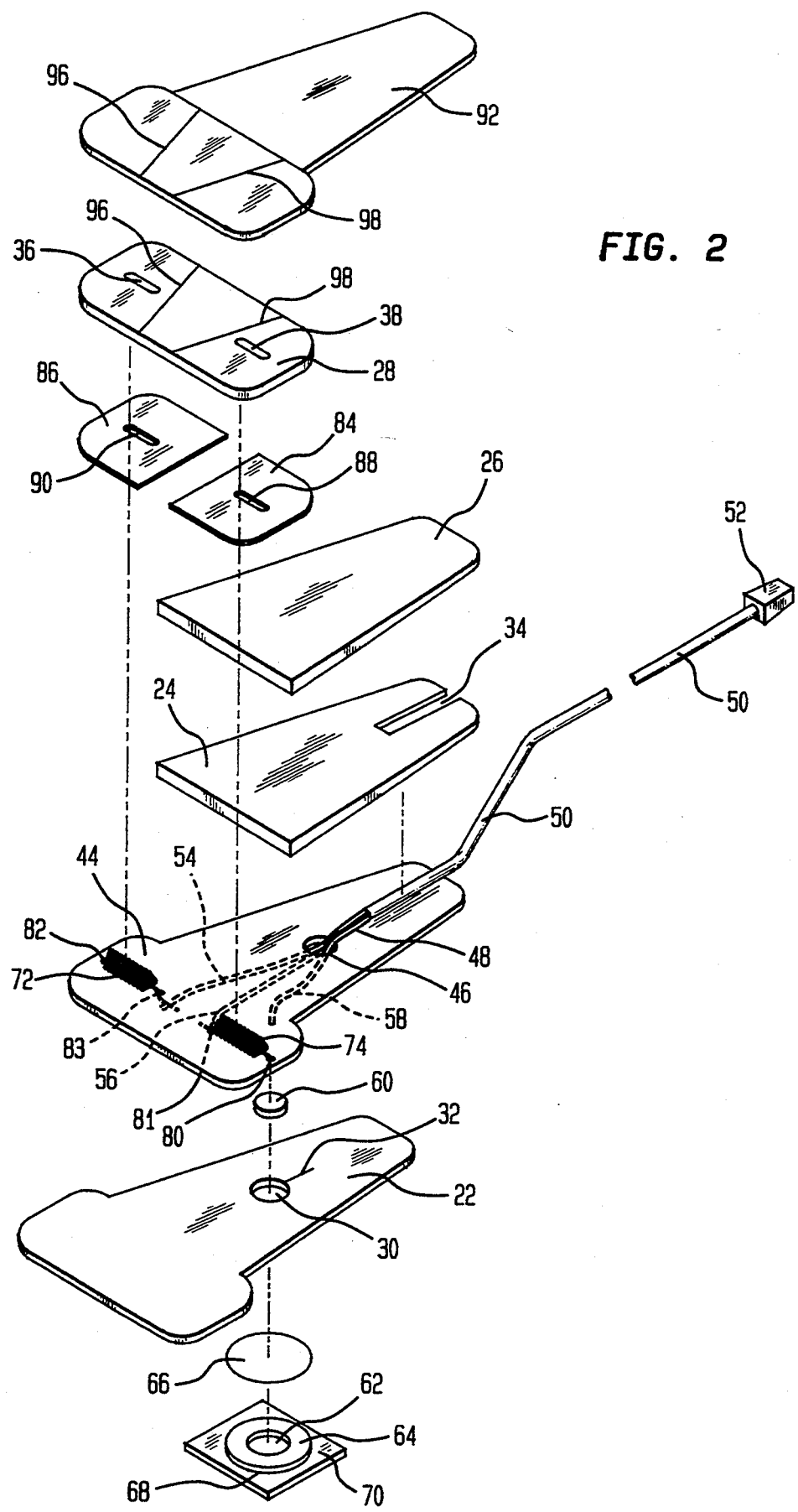
FIG. 2 is a perspective, exploded view of a disassembled electrode assembly of the present invention.

As shown in FIG. 2, electrode assembly 10 includes four pads 22, 24, 26, and 28. Each of pads 22, 24, 26, and 28 is preferably made of a low cost, soft, pliable material which comfortably contacts the skin of a patient. Medical grade copolymer foam is suitable.

The lower pad 22 has a medical grade pressure sensitive adhesive on its top surface and no adhesive on its bottom surface. A central, preferably circular, opening 30 is provided in lower pad 22. A slit 32 extends away from opening 30. Lower pad 22 is preferably about 0.0625 inches (1.6 mm) thick and has the "T" shape of leg plate 20, forming one layer of leg 40 and head 42 of leg plate 20.

A first trapezoidal-shaped pad 24 is provided with a notch 34. Notch 34 receives cord 50. A second trapezoidal-shaped pad 26 is also provided. Second trapezoidal-shaped pad 26 does not have a notch; therefore, it extends over and covers a portion of cord 50. Each of the first and second trapezoidal-shaped pads 24, 26 is preferably about 0.0625 inches (1.6 mm) thick and each may have a medical grade pressure sensitive adhesive on its top, its bottom, or both surfaces. First and second trapezoidal-shaped pads 24, 26 partially form leg 40 of leg plate 20.

Pad 28 has a medical grade pressure sensitive adhesive on its bottom surface. Having a substantially rectangular shape, pad 28 partially forms head 42 of leg plate 20. Two, substantially rectangular catches 36 and 38 are formed in pad 28. Pad 28 is preferably about 0.125 inches (3.2 mm) thick. The thickness and shape of pad 28 are such that, when pad 28 is combined with first and second trapezoidal-shaped pads 24 and 26, pad 28 and first and second trapezoidal-shaped pads 24 and 26 form a second layer of leg 40 and head 42 of leg plate 20.

A thin, clear, plastic plate 44 is provided over lower pad 22. Plate 44 may be made of polyester, treated to assure adhesion to lower pad 22 and first trapezoidal-shaped pad 24, and is about 0.010 inches (0.25 mm) thick. Plate 44 has approximately the same dimensions as lower pad 22. When placed over and pressed against lower pad 22, plate 44 adheres to the top surface of lower pad 22. Plate 44 has a hole 46 and a slot 48 which correspond to and are aligned with opening 30 and slit 32, respectively, in lower pad 22.

Cord 50 consists of at least three, separate wires 54, 56, and 58. Cord 50 is positioned between plate 44 and first trapezoidal-shaped pad 24, resting on top of plate 44. The adhesive on the bottom surface of first trapezoidal-shaped pad 24 holds wires 54, 56, and 58 and cord 50 in position. Third wire 58 of cord 50 runs freely through hole 46 in plate 44 and opening 30 in lower pad 22. The end of third wire 58 opposite cord 50 is attached to a conductive eyelet 60. In the preferred embodiment, conductive eyelet 60 has a plastic body coated with silver/silver chloride; as known to those persons skilled in the art, most any suitable conductive material would suffice for conductive eyelet 60.

Conductive eyelet 60 is positioned in a correspondingly shaped aperture 62 in a thin, foam layer 64. A thin, insulating, plastic lid 66 having one adhesive coated side is placed over the junction between third wire 58 and conductive eyelet 60 to protect the electrical and mechanical attachment and to secure conductive eyelet 60 in aperture 62 of layer 64 so that the bottom surface of conductive eyelet 60 protrudes slightly from the bottom surface of layer 64.

To enhance ion conductivity between conductive eyelet 60 and the patient, a conductive gel 68 covers the portion of conductive eyelet 60 protruding from the lower surface of layer 64. Conductive eyelet 60 and conductive gel 68 together form the reference electrode. Conductive gel 68, in the preferred embodiment a tacky (gently adhesive) hydrogel, is protected by a removeable cover 70 until electrode assembly 10 is put into use. Conductive gel 68 is preferably solid, non-irritating, translucent, and adhesive.

Conductive eyelet 60 is insulated from above by insulating lid 66 which covers aperture 62 in layer 64 on its upper surface. Insulating lid 66 is flexible. In the preferred embodiment, insulating lid 66 is vinyl. As known by those skilled in the art, however, most any suitable insulating material would suffice.

Figure 3:
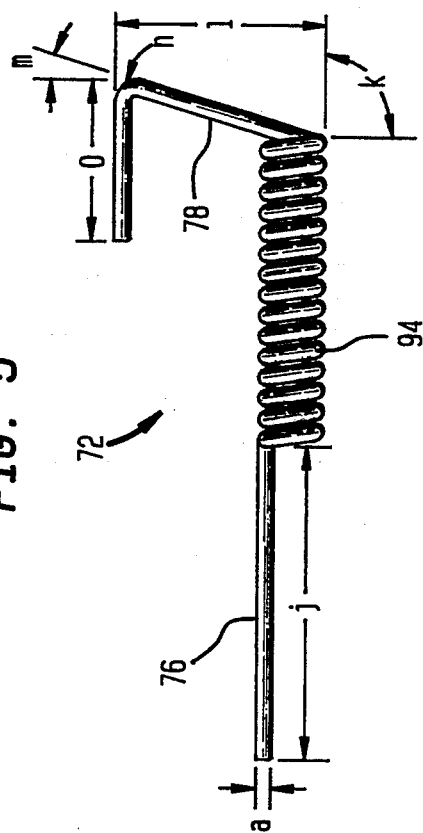
FIG. 3 is a side view of an electrode assembly of the present invention, illustrating the floating maternal reference electrode.

As shown best in FIG. 3, third wire 58 runs through hole 46 in plate 44 and opening 30 in lower pad 22 and extends freely below the surface of lower pad 22. Moreover, third wire 58 is free to traverse slot 48 in plate 44 and corresponding slit 32 in lower pad 22. Conductive eyelet 60, positioned in layer 64, is attached to the end of third wire 58. Because it is not fixed to electrode assembly 10 in a single position, conductive eyelet 60 forming the reference electrode is free to "float" or to move with the patient. That freedom minimizes motion artifacts which would otherwise arise as the patient moves relative to a fixed reference electrode.

Affixed to plate 44 are a pair of triangular shaped springs 72 and 74. Each spring 72, 74 has a first arm 76 and a second arm 78. First wire 54 of cord 50 is attached to first arm 76 of first spring 72; similarly, second wire 56 of cord 50 is attached to first arm 76 of second spring 74. Springs 72, 74 rest on the top surface of plate 44. Arms 76, 78 of each spring 72, 74 pass through a pair of openings (81, 80 for spring 74 and 83, 82 for spring 72) in plate 44 and extend underneath plate 44 to affix springs 72, 74 to plate 44.

A pair of plastic tabs 84 and 86 are affixed to the bottom surface of pad 28 facing springs 72, 74 and plate 44. Each tab 84, 86 is a thin piece of plastic approximately 1 inch (2.5 cm) square. Tabs 84, 86 may be made of polyester, treated to assure adhesion to pad 28, and are about 0.010 inches (0.25 mm) thick. A substantially rectangular catch 88 is formed in tab 84; similarly, a substantially rectangular catch 90 is formed in tab 86. Catches 88 and 90 in tabs 84 and 86 align with catches 36 and 38 formed in pad 28.

Finally, a label 92 is provided as the top layer of leg plate 20. Label 92 has the "T" shape of leg plate 20, forming the top layer of leg 40 and head 42 of leg plate 20, and will accept printed indicia 106 (as shown best in FIG. 7). Preferably formed of a flexible vinyl material, label 92 is adhered to the top surfaces of pad 28 and second trapezoidal-shaped pad 26.

Springs 72 and 74 electrically and mechanically connect leads 16 and 18 to electrode assembly 10. Springs 72 and 74 are made of a conducting material, preferably stainless steel. Because first wire 54 of cord 50 is attached to first spring 72 and second wire 56 of cord 50 is attached to second spring 74, springs 72 and 74 complete the electrical path from the fetus to fetal monitor 12.

Figure 4:
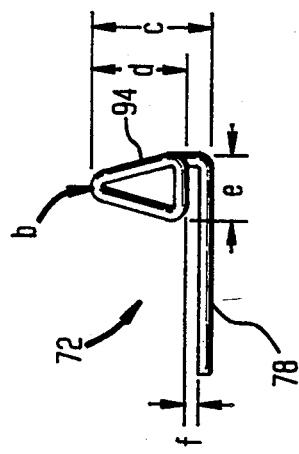
FIG. 4 is a side view of the triangular spring incorporated in the electrode assembly of the present invention to electrically and mechanically connect the fetal electrode lead wires to the assembly.
Figure 5:
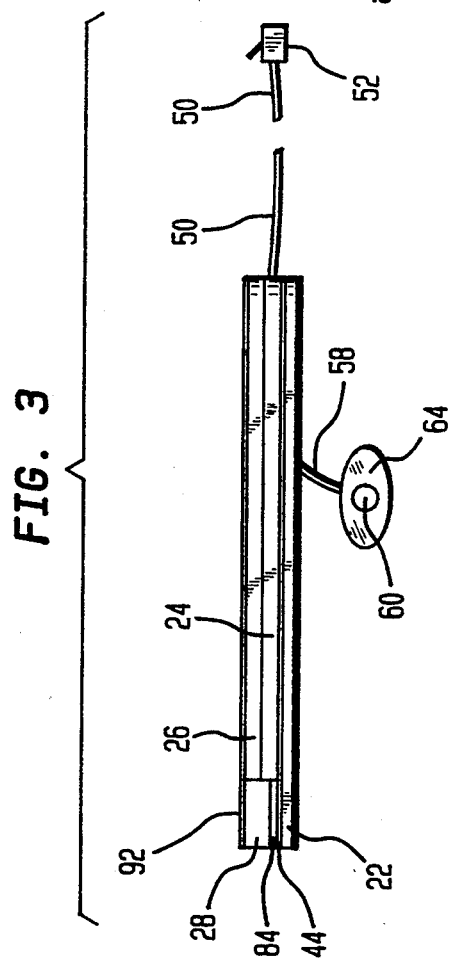
FIG. 5 is a top view of the triangular spring shown in FIG. 4.
Figure 6:
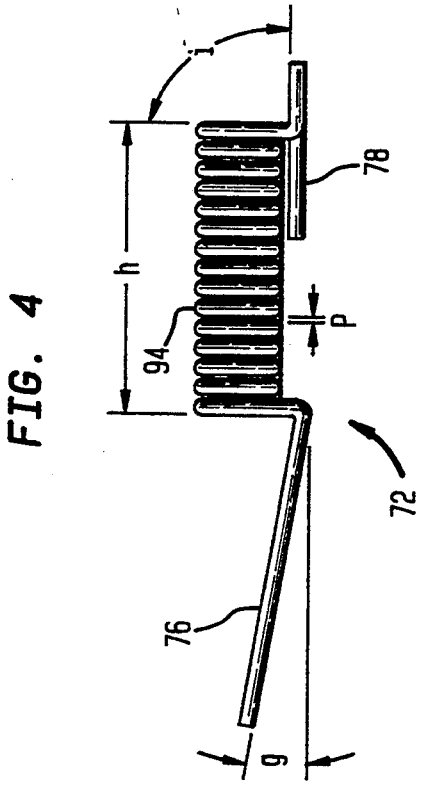
FIG. 6 is an end view of the triangular spring shown in FIGS. 4 and 5.
Figure 8:
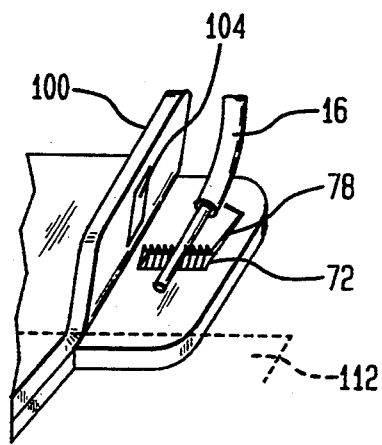
FIG. 8 is a perspective view showing the engagement between a fetal electrode lead wire and the triangular spring.
Figure 9:
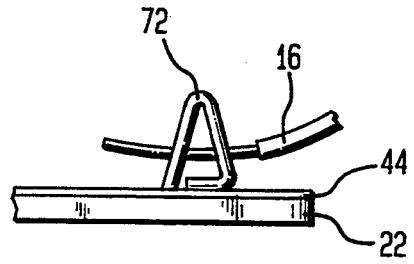
FIG. 9 is an end view of the engagement shown in FIG. 8.

As shown in FIGS. 4, 5, and 6, and using first spring 72 as the example (second spring 74 may be the mirror image of first spring 72), spring 72 has a plurality of somewhat flexible coils 94. The diameter a of spring 72 is about 0.015 inches (0.38 mm). Each coil is separated by a small distance p of about 0.0125 inches (0.32 mm). This distance is sufficient to wedge an uninsulated end of lead 16 between adjacent coils 94 (as shown in FIGS. 8 and 9). To facilitate attachment of lead 16 to spring 72, coils 94 are disposed vertically and horizontally; thus, angles i and k are each about ninety degrees. Coils 94 of spring 72 cover a length h of about 0.385 inches (9.8 mm). The dimensions of springs 72, 74 are chosen to assure ease of use.

Electrode assembly 10 must have a low profile. Accordingly, the total height c of spring 72 is small: on the order of 0.15 inches (3.8 mm). The height d of each coil 94 is about 0.125 inches (3.2 mm). In addition, each coil 94 has a width e of about 0.08 inches (2 mm). The top bend in each coil 94 has a radius of curvature b of about 0.02 inches (0.5 mm).

First arm 76 and second arm 78 of spring 72 hold spring 72 in place on plate 44. First arm 76, which has a length j of about 0.50 inches (12.7 mm), is formed at an angle g of about ten degrees from the horizontal (see FIG. 4). After first arm 76 is pushed through first opening 83 in plate 44, first arm 76 springs upwardly against the bottom of plate 44. Thus, first arm 76 holds spring 72 fast against plate 44.

Second arm 78 of spring 72 lies substantially in the horizontal plane and extends from coils 94 at an angle m of about 25 degrees. Second arm 78 extends a horizontal distance l of about 0.28 inches (7.1 mm), makes a bend n having a radius of curvature of about 0.03 inches (0.7 mm), and extends parallel to the longitudinal axis of coils 94 a distance o of about 0.25 inches (6.4 mm). This configuration assures that second arm 78 will securely fasten spring 72 to plate 44 after passing through opening 82 in plate 44.

Second arm 78 extends below the level of coils 94 by a distance f of about 0.01 inches (0.25 mm) (see FIG. 6). Thus, after second arm 78 is pushed through second opening 82 in plate 44, plate 44 (which has a thickness of about 0.01 inches or 0.25 mm) is wedged snugly between the bottom of coils 94 and second arm 78.

When plate 44 is pushed against the adhesive top surface of lower pad 22, first arm 76 and second arm 78 of spring 72 are trapped between plate 44 and lower pad 22. Thus, spring 72 is fixed in position. As illustrated in FIG. 5, the helix of spring 72 is formed in the bottom of spring 72. This increases the stability of spring 72 and makes it easier to engage lead 16.

Pad 28 and label 92 may be bent along hinge lines 96 and 98 to form flaps 100 and 102. Flaps 100 and 102 rotate about hinge lines 96 and 98 between a closed position (see FIG. 7) and an open position (see FIG. 8). Catch 36 in pad 28 and corresponding catch 90 in tab 86 combine to form latch 104 in flap 100. Similarly, catch 38 in pad 28 and corresponding catch 88 in tab 84 combine to form a second latch (not shown). The second latch is identical to first latch 104. Tabs 84 and 86 provide rigidity and structure to the latches.

Latch 104 is sized to snap over first spring 72 snugly via an interference fit. Consequently, when flap 100 is rotated from its open position to its closed position, latch 104 forces lead 16 downward between adjacent coils 94 of spring 72. Latch 104 holds tab 86 against plate 44 and holds lead 16 in contact with spring 72 (with the assistance of the wedging action provided by coils 94). The second latch (not shown) similarly holds tab 84 against plate 44 and holds lead 18 in contact with spring 72.

Consequently, no adhesive is used to attach leads 16 and 18 to electrode assembly 10. This permits the user to remove and reattach leads 16 and 18 easily—as required to reposition the leads. It is relatively difficult to reposition leads 16 and 18 when adhesive is used to attach leads 16 and 18 to electrode assembly 10.

As stated above, label 92 will accept printed material including indicia 106 such as writing, printing, or the like. Label 92 provides a functional advantage because it depicts the proper orientation of leads 16 and 18 relative to electrode assembly 10. Lead 16 is typically red and lead 18 is typically green. Leads 16 and 18 should be disposed perpendicularly to first spring 72 and second spring 74, respectively, to which leads 16 and 18 will be attached. Consequently, label 92 has a red line 108 drawn on flap 100 perpendicular to spring 72 and a green line 110 drawn on flap 102 perpendicular to spring 74.

Applied over the top surface of label 92 are the structural elements necessary to attach electrode assembly 10 to the patient. Many structural elements are possible to perform the attachment function, as would be known by those persons skilled in the art.

In U.S. Pat. No. 5,197,472, DiSabito discloses one or more Velcro ® strips affixed to the upper surface of the electrode assembly. An adjustable belt, one side of which is formed of a material which sticks to the Velcro ® strips, is used to attach the electrode assembly to a patient without using a skin-contacting adhesive. DiSabito also discloses belt loops, which could be formed on the upper surface of the electrode assembly, into which a strap could be inserted.

A foam strap having a medical grade pressure sensitive adhesive on its surface might also be used; the adhesive surface should be protected by a cover or liner before use. Tape is also suitable.

Whether the attachment member 112 is a belt, strap, tape, or other similar structure, the width of member 112 should be about 1.75 inches (44.5 mm). This allows member 112 to be placed over leg 40 of leg plate 20 and not interfere with flaps 100 and 102 on head 42. The length of member 112 should be sufficient to affix electrode assembly 10 to the patient.

Electrode assembly 10 has no sharp edges or exposed wires. It does not incorporate hard or bulky components. Therefore, electrode assembly 10 is safe and comfortable for the patient. It also has a relatively low profile: electrode assembly 10 is about 5 mm in height.

The electrode assembly 10 described above is used in the following manner. First, the removable cover 70 protecting conductive gel 68 on conductive eyelet 60 is removed, thus exposing the conductive gel. Conductive eyelet 60 is placed on a selected site on the patient, which may be the upper thigh, the abdomen, or some other site. Then leg plate 20 is attached to the patient by way of attachment member 112. Care is necessary when using attachment member 112 to assure that flaps 100 and 102 are exposed and can rotate about hinge lines 96 and 98. After the fetal electrode has been applied to the fetus, leads 16 and 18 extending from the fetus are aligned (perpendicular to springs 72 and 74) with the appropriate lines 108 and 110 on label 92.

Subsequently, flaps 100 and 102 are rotated into their open positions to expose springs 72 and 74. Leads 16 and 18 are inserted between adjacent coils 94 of springs 72 and 74. Flaps 100 and 102 are rotated into their closed positions and pressed firmly against plate 44 and lower pad 22. Latch 104 holds lead 16 in contact with spring 72 and maintains tab 86 against plate 44. The second latch similarly maintains tab 84 against plate 44 and holds lead 18 in contact with spring 72.

The remaining step is to connect electrode assembly 10 to fetal monitoring device 12. That connection is made through cord 50 and plug 52 by inserting plug 52 into fetal monitoring device 12 or into an extension cable 14 connected to that device. Preferably, for economic reasons, extension cable 14 is used.

It should be readily apparent that electrode assembly 10 can be made relatively inexpensively. Consequently, electrode assembly 10 can be used once and discarded; it is disposable.

Although the present invention has been described with specific reference for use with a fetal monitoring device, it should be readily apparent that the invention may have numerous other uses. For example, the electrode assembly could be used with the appropriate equipment to produce an electrocardiogram. If so used, the maternal reference electrode of electrode assembly 10 itself will function as one of the body electrodes. The wires leading to other electrodes placed on other parts of the patient's body would be connected to electrode assembly 10 at springs 72 and 74.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A disposable electrode assembly for contacting a patient and for receiving electrical signals from at least one remotely located electrode, said remotely located electrode having leads and said electrode assembly comprising:

a thin, flexible, leg plate having a bottom surface for contacting said patient without adhesive;

means carried by said leg plate for electrically and mechanically connecting said leads from said at least one remotely located electrode to said leg plate;

a reference electrode adapted to be in electrical contact with said patient through a skin-contacting surface when said electrode assembly is secured to said patient, said reference electrode electrically coupled to and mechanically decoupled from said leg plate;

separate, insulated wires electrically engaging said connecting means and said reference electrode;

a cord joining said separate wires and providing electrical connection to an external monitoring device; and means for attaching said electrode assembly to said patient.

2. A disposable electrode assembly as claimed in claim 1 wherein said reference electrode has a thin layer of conductive gel covering said skin-contacting surface of said reference electrode for enhancing ion conductivity between said reference electrode and said patient.

3. A disposable electrode assembly as claimed in claim 2 wherein said gel is hydrogel.

4. A disposable electrode assembly as claimed in claim 2 further comprising a removable cover protecting said thin layer of gel before use.

5. A disposable electrode assembly as claimed in claim 1 wherein said reference electrode has a silver/silver chloride coating.

6. A disposable electrode assembly as claimed in claim 1 further comprising a foam layer having an aperture and a bottom surface for contacting said patient, said reference electrode disposed in said aperture of said foam layer so that said reference electrode protrudes slightly below said bottom surface of said foam layer.

7. A disposable electrode assembly as claimed in claim 6 further comprising an insulating lid, said reference electrode having a surface opposite its skin-contacting surface and said insulating lid covering said opposing surface.

8. A disposable electrode assembly for contacting a patient and for receiving electrical signals from at least one remotely located electrode, said remotely located electrode having leads and said electrode assembly comprising:

a thin, flexible, leg plate having a bottom surface for contacting said patient without adhesive;

at least two triangular-shaped springs carried by said leg plate for electrically and mechanically connecting said leads from said at least one remotely located electrode to said leg plate;

at least two latches formed in said leg plate each adapted to snap over one of said triangular-shaped springs;

a reference electrode adapted to be in electrical contact with said patient through a skin-contacting surface when said electrode assembly is secured to said patient;

separate, insulated wires electrically and mechanically engaging said springs and said reference electrode;

a cord joining said separate wires and providing electrical connection to an external monitoring device; and means for attaching said electrode assembly to said patient.

9. A disposable electrode assembly as claimed in claim 8 wherein said springs have a plurality of flexible coils adapted to wedge said leads from said at least one remotely located electrode between said coils.

10. A disposable electrode assembly for contacting a patient and for receiving electrical signals from at least one remotely located electrode, said remotely located electrode having leads and said electrode assembly comprising:

a thin, flexible, leg plate having a bottom surface for contacting said patient without adhesive;

at least two triangular-shaped springs carried by said leg plate for electrically and mechanically connecting said leads from said at least one remotely located electrode to said leg plate;

at least two latches formed in said leg plate each adapted to snap over one of said triangular-shaped springs;

a reference electrode adapted to be in electrical contact with said patient through a skin-contacting surface when said electrode assembly is secured to said patient, said reference electrode electrically coupled to and mechanically decoupled from said leg plate;

separate, insulated wires electrically engaging said springs and said reference electrode;

a cord joining said separate wires and providing electrical connection to an external monitoring device; and means for attaching said electrode assembly to said patient.

11. A disposable electrode assembly as claimed in claim 10 wherein said reference electrode has a thin layer of conductive gel covering said skin-contacting surface of said reference electrode for enhancing ion conductivity between said reference electrode and said patient.

12. A disposable electrode assembly as claimed in claim 11 wherein said gel is hydrogel.

13. A disposable electrode assembly as claimed in claim 11 further comprising a removable cover protecting said thin layer of gel before use.

14. A disposable electrode assembly as claimed in claim 10 wherein said reference electrode has a silver/silver chloride coating.

15. A disposable electrode assembly as claimed in claim 10 further comprising a foam layer having an aperture and a bottom surface for contacting said patient, said reference electrode disposed in said aperture of said foam layer so that said reference electrode protrudes slightly below said bottom surface of said foam layer.

16. A disposable electrode assembly as claimed in claim 15 further comprising an insulating lid, said reference electrode having a surface opposite its skin-contacting surface and said insulating lid covering said opposing surface.

17. A disposable electrode assembly as claimed in claim 10 wherein said springs have a plurality of flexible coils adapted to wedge said leads from said at least one remotely located electrode between said coils.

18. A disposable electrode assembly as claimed in claim 10 wherein said leg plate has a "T" shape formed by a substantially trapezoidal, tapered leg and a substantially rectangular head disposed perpendicularly to said leg.

19. A disposable electrode assembly as claimed in claim 10 wherein said leg plate has:
 a lower pad having a top surface with adhesive and a bottom surface without adhesive, said bottom surface of said lower pad forming said bottom surface of said leg plate for contacting said patient without adhesive;
 a non-conductive plate adhered to said lower pad by said adhesive on said top surface of said lower pad;
 a first trapezoidal-shaped pad having a bottom surface with adhesive and a top surface, said first trapezoidal-shaped pad adhered to said non-conductive plate by said adhesive on said bottom surface of said first trapezoidal-shaped pad;
 a second trapezoidal-shaped pad having a bottom surface with adhesive and a top surface, said second trapezoidal-shaped pad adhered to said top surface of said first trapezoidal-shaped pad;
 a fourth pad having a bottom surface with adhesive and a top surface and disposed adjacent both said first and said second trapezoidal-shaped pads, said fourth pad adhered along a portion of said fourth pad to said non-conductive plate by said adhesive on said bottom surface of said fourth pad;
 a pair of non-conductive tabs adhered to said fourth pad, on opposite sides of said portion of said fourth pad adhered to said non-conductive plate, by said adhesive on said bottom surface of said fourth pad; and
 a label adhered to said top surface of said fourth pad and to said top surface of said second trapezoidal-shaped pad.

20. A disposable electrode assembly as claimed in claim 19 wherein said lower pad, said first trapezoidal-shaped pad, said second trapezoidal-shaped pad, and said fourth pad are copolymer foam.

21. A disposable electrode assembly as claimed in claim 19 wherein said lower pad has an opening and a slit extending away from said opening and said non-conductive plate has a hole aligned with said opening in said lower pad and a slot aligned with said slit in said lower pad.

22. A disposable electrode assembly as claimed in claim 21 wherein said insulated wires lie, and are adhesively held in position, between said non-conductive plate and said first trapezoidal-shaped pad.

23. A disposable electrode assembly as claimed in claim 22 wherein said insulating wire engaging said reference electrode runs freely through said hole in said non-conductive plate and said opening in said lower pad and traverses said slot in said non-conductive plate and said slit in said lower pad.

24. A disposable electrode assembly as claimed in claim 19 wherein said first trapezoidal-shaped pad has a notch receiving said cord and said second trapezoidal-shaped pad covers a portion of said cord.

25. A disposable electrode assembly as claimed in claim 19 wherein said electrode assembly has a height of approximately 5 mm.

26. A disposable electrode assembly as claimed in claim 19 wherein said springs are affixed to said non-conductive plate.

27. A disposable electrode assembly as claimed in claim 26 wherein said springs are stainless steel.

28. A disposable electrode assembly as claimed in claim 19 wherein said fourth pad and said label have hinge lines forming a pair of flaps adapted to rotate about said hinge lines between an open position exposing said springs and a closed position covering said springs.

29. A disposable electrode assembly as claimed in claim 28 wherein one of said latches is formed in each of said flaps.

30. A disposable electrode assembly as claimed in claim 29 wherein said latches are formed by catches in said tabs and in said fourth pad.

31. A disposable electrode assembly as claimed in claim 19 wherein said label has indicia depicting the orientation of said leads from said remotely located electrode relative to said electrode assembly.

* * * * *